US012589011B2

(12) United States Patent  
Ledinger et al.

(10) Patent No.: US 12,589,011 B2  
(45) Date of Patent: Mar. 31, 2026

(54) PROSTHETIC HAND

(71) Applicant: OTTO BOCK HEALTHCARE PRODUCTS GMBH, Vienna (AT)

(72) Inventors: Christoph Ledinger, Möllersdorf (AT); Luis Sagmeister, Pitten (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 614 days.

(21) Appl. No.: 18/001,426

(22) PCT Filed: Jun. 11, 2021

(86) PCT No.: PCT/EP2021/065760  
§ 371 (c)(1),  
(2) Date: Dec. 9, 2022

(87) PCT Pub. No.: WO2021/250233  
PCT Pub. Date: Dec. 16, 2021

(65) Prior Publication Data  
US 2023/0201006 A1     Jun. 29, 2023

(30) Foreign Application Priority Data  
Jun. 12, 2020     (DE) ..................... 10 2020 115 575.1

(51) Int. Cl.  
*A61F 2/58*          (2006.01)  
*A61F 2/76*          (2006.01)  
(52) U.S. Cl.  
CPC ................ *A61F 2/586* (2013.01); *A61F 2/76* (2013.01)

(58) Field of Classification Search  
CPC ............ A61F 2/583; A61F 2002/30515; A61F 2002/30428; A61F 2002/30479; A61F 2/58; A61F 2/54; A61F 2002/587  
See application file for complete search history.

(56) References Cited

U.S. PATENT DOCUMENTS

| | | | |
|---|---|---|---|
| 6,231,618 B1 * | 5/2001 | Schall ....................... | A61F 2/76 623/53 |
| 2007/0260328 A1 | 11/2007 | Bertels et al. | |
| 2019/0183661 A1 | 6/2019 | Gill | |
| 2023/0201006 A1 * | 6/2023 | Ledinger ................... | A61F 2/76 623/57 |

FOREIGN PATENT DOCUMENTS

CN          101069658 A     11/2007

\* cited by examiner

*Primary Examiner* — Bruce E Snow  
(74) *Attorney, Agent, or Firm* — WCF IP

(57) ABSTRACT

A prosthetic hand with a chassis (20) and at least one base element (10) for fastening a prosthetic finger to the chassis (20), wherein a longitudinal guide for the base element (10) is arranged or formed on the chassis (20), the base element (10) being mounted in said longitudinal guide, wherein the longitudinal guide blocks two translational degrees of freedom and a clamping element (30) is assigned to the longitudinal guide, said clamping element being displaceably mounted in or on the chassis (20) or the base element (10) between a locking position and an unlocking position and effecting a blocking of the third translational degree of freedom in the locking position.

20 Claims, 5 Drawing Sheets

PROSTHETIC HAND

Figure 1:
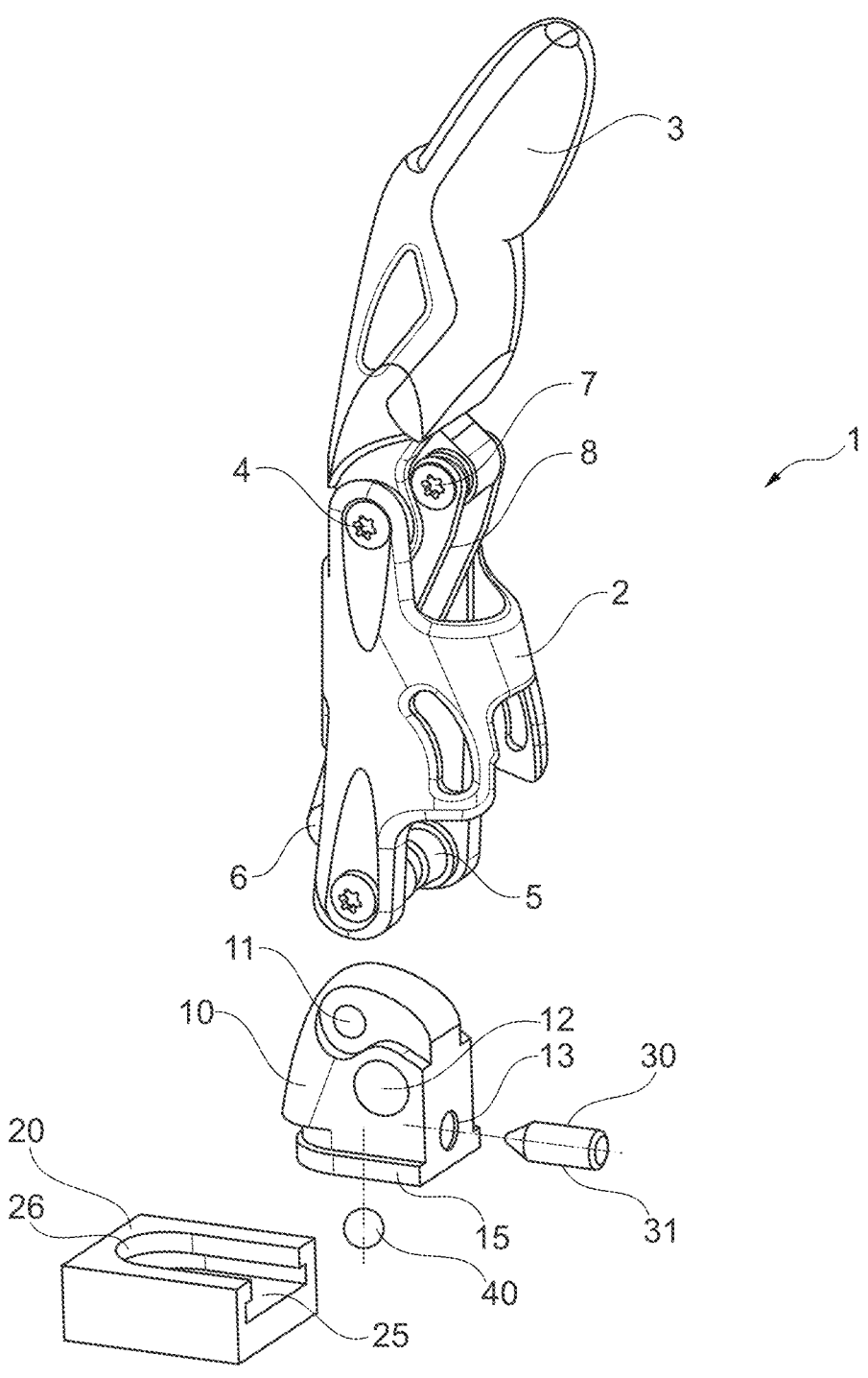

The invention relates to a prosthetic hand having a chassis and at least one base element for attaching a prosthetic finger to the chassis.

Prosthetic hands are used for prosthetic treatment of an upper limb. A prosthetic hand is arranged on a forearm socket or a forearm tube to replicate at least one function of a natural hand to provide a patient with enhanced functionality. Typically, this functionality is a grasping function. For this purpose, a gripping element is movably mounted on a chassis or a base body and can be moved by a drive device. In addition to mechanical actuation, for example via a traction means activated by a shoulder movement, in modern prosthetic devices gripping elements or prosthetic fingers are mounted on a chassis driven by at least one motor drive. The gripping devices or prosthetic fingers themselves may be articulated to provide functionality approximating that of a natural finger. One or more finger joints may be formed in the prosthetic fingers so that during a closing movement or when the fingers move toward the palm, they are flexed. The prosthetic fingers are mainly mounted to the chassis at their proximal ends for displacement about a pivot axis.

The respective drives for displacing the prosthetic fingers relative to the chassis or the finger elements relative to each other are often located in the chassis, which is reminiscent in its basic shape of the palm of a natural hand. The prosthetic fingers are attached to the chassis in a variety of ways, predominantly via a hinge joint formed on the chassis. An axle is inserted through two bearing blocks on the finger or chassis and locks them into a bearing pin or bearing washer on the other component. Such arrangements are problematic in terms of both mounting and removing the individual prosthetic fingers. In addition, there are difficulties regarding sealing as well as durability.

Prosthetic hands from the prior art are described, for example, in DE 10 2014 005 528 A1, US 2014/107805 A1 or US 2013/305984 A1.

The task of the present invention is to provide a prosthetic hand in which the prosthetic fingers are easier to mount and replace.

According to the invention, this task is solved by a prosthetic hand having the features of the main claim. Advantageous embodiments and further developments of the invention are disclosed in the subclaims, the description and the figures.

The prosthetic hand with a chassis and at least one base element for fastening a prosthetic finger to the chassis provides that a longitudinal guide for the base element is arranged or formed on the chassis, in which the base element is mounted, wherein the longitudinal guide blocks two translational degrees of freedom and a clamping element is assigned to the longitudinal guide, said clamping element being displaceably mounted in or on the chassis or the base element between a locking position and an unlocking position and effects a blocking of the third translational degree of freedom in the locking position. A longitudinal guide is formed by a groove and a tongue which have corresponding cross-sections and on which different components are arranged or formed, i.e. the groove on the chassis and the tongue on the base element or vice versa. By arranging the base element in a longitudinal guide with only one translational degree of freedom and a clamping element that locks the third translational degree of freedom in the locking position of the clamping element, it is possible to quickly and easily assemble and disassemble the base element and thus also the prosthetic finger, which is attached, in particular rotatably mounted, to the base element. All that is required for this is the actuation of a clamping element, which can be arranged as a preassembled part either on the chassis or on the finger unit consisting of base element and prosthetic finger. The clamping element acts on the base element and locks the third translational degree of freedom or releases it again. Therefore, only the clamping element needs to be moved from the locking position to the unlocking position or vice versa in order to be able to remove a prosthetic finger from the prosthetic hand or fix it to it. No other components need to be disassembled to install or remove the base element and the prosthetic finger. In particular, if the clamping element is movably or displaceably fixed in the chassis or in the base element, it cannot be lost even in the dismantled state; the clamping element is thus a component of the base element or of the chassis and remains attached thereto in the dismantled state.

A further embodiment of the invention provides that the clamping element acts on at least one locking element and brings the latter from an unlocking position into a locking position. A locking element is acted upon via the clamping element, which can be operably mounted or fixed to the chassis or the base element, ultimately preventing relative displacement between the base element and the chassis. In one position of the clamping element, in the unlocked position, the locking element is also in the unlocked position: when the clamping element is brought into the locked position, it displaces the locking element from the unlocking position into the locking position and fixes the base element in the longitudinal guide to the chassis.

The clamping element or the locking element may clamp the base element in the longitudinal guide, for example by pressing or clamping the tongue, which may be formed on the chassis or the base element, against a groove wall within the groove. Alternatively or additionally, a form-fit of the clamping element or the locking element may occur so that the base element is locked in the longitudinal guide. For example, a recess or form-fit element can be formed in a groove wall or on a part of the tongue, in which the clamping element or locking element engages in the locking position. Together with the form-fit, it is possible for transverse forces to be applied perpendicular to at least one of the two always locked translational degrees of freedom, thus providing a clamping effect in addition to the form-fit components.

The longitudinal guide can be designed as a T-guide, L-guide, cylindrical guide or dovetail guide; in general, all geometries with undercuts that lock two translational degrees of freedom are suitable for the longitudinal guide. The longitudinal guide allows the base element and thus the prosthetic finger to be mounted in precise alignment with the chassis and with each other. If the components of the longitudinal guide are clamped against each other, the manufacturing tolerances can be chosen to be comparatively large, since the design of the longitudinal guide is insensitive to dimensional deviations or geometric misalignments.

A further embodiment of the invention provides that the chassis is designed to be disc-like and the longitudinal guide has an orientation that is orthogonal to the major surface of the disc-like chassis. In particular, if several or all of the prosthesis fingers are mounted on the chassis in this manner, it renders assembly easier since all of the base elements and thus also the prosthesis fingers are oriented in a common joining direction. The orientation of the chassis corresponds essentially to the palm of a natural hand, and the assembly direction then takes place from the palm to the back of the hand or from the back of the hand to the palm, i.e. either in the dorsal direction or in the volar direction.

The longitudinal guide can have an end stop so that the orientation of the base element and thus also of the prosthetic fingers in the volar direction or dorsal direction can be clearly defined. This enables several prosthetic fingers to always be fixed to the chassis in the correct orientation to each other. If the groove of the longitudinal guide is located on the chassis, the groove has only one insertion opening and the other end of the groove is closed or provided with a catch, so that after the tongue, which in this example is formed or arranged on the base element, has been fully inserted, the base element is located in the correct position. Alternatively, it is possible that an end stop is formed on the tongue, for example a cross bolt or a wall, so that the tongue cannot be inserted further into the groove, which can then also be formed continuously. In principle, it is also possible to form or arrange an end stop at opposite ends of the groove and the tongue respectively, so that the longitudinal guide is closed or sealed from the outside. Seals can be arranged at the end stops to prevent or at least impede the penetration of dirt.

A further embodiment of the invention provides that the base element has a bearing block for the respective prosthetic finger. A bearing point for the prosthetic finger can be arranged or formed on the base element, so that pivoting can take place relative to the base element and, after the base element has been fixed to the chassis, also relative to the chassis. The base element and the respective prosthetic finger arranged thereon thus form a module that can be jointly fixed to the chassis or removed from the chassis.

The locking element can be displaceably mounted along the longitudinal extension of the longitudinal guide, resulting in facilitated accessibility and ease of marking. The tongue is inserted into the groove of the longitudinal guide along the longitudinal extension of the longitudinal guide. Displacement of the clamping element takes place in the same direction, which then results in clamping or locking of the longitudinal guide in the direction of insertion and against the direction of insertion. If the longitudinal guides are oriented perpendicular to a main plane of the chassis, several finger elements can be inserted into the base elements, for example, from the palm of the hand, and the clamping element can be displaced in the same orientation. This simplifies assembly and disassembly, since immediate locking and unlocking of the attachment of the respective prosthetic finger or base element to be disassembled or attached can take place.

The clamping element can be designed as a screw or with a screw or can be coupled with a screw. The design as a screw enables the clamping element to be actuated with simple, conventional tools. The clamping element itself remains in the thread even in the disassembled state so that it cannot be lost. All that is required is the actuation of a single, standardized element with standardized tools, without the need for any other material such as washers, bolts, pins or clips. In principle, it is also possible for the clamping element to be inclined or oriented transversely to the longitudinal extension of the longitudinal guide, whereby direct form-fitting or clamping locking can be achieved by the clamping element. Provided that the clamping element acts on at least one locking element, the latter can be brought into a form-fit position or a clamping locking position by displacing the clamping element formed as a screw.

The clamping element or locking element, if present, can be assigned a recess in which it engages in the locking position. The engagement can be purely form-fit, for example by displacing or moving the clamping element or locking element into the recess; alternatively or additionally, a force can be exerted by the clamping element or locking element into the recess or on the carrier of the recess, by means of which a supporting clamping and simultaneous compensation of play takes place. If the locking element is in the chassis, the recess is formed in the base part and vice versa.

Advantageously, the recess is arranged at a position in the groove or on the tongue of the longitudinal guide in which the base element on the chassis assumes its end position. Only when the end position is reached can the clamping element or locking element engage in the recess. With a play-compensating and self-centering design of the recess and the corresponding clamping element or locking element, it is possible for the base element on the chassis to be moved into its end position by introducing and inserting the clamping element or locking element into the recess. This can be achieved by a spherical or conical or otherwise beveled design of at least one of the two connecting partners, for example by a dome-shaped design of the recess and a spherical design of the clamping element or locking element. Even with a wedge-shaped design of the locking element and a right-angled groove as recess, such an additional clamping action can take place in the longitudinal extension in order to move the base element on the chassis into its end position and hold it clamped in the end position. Similarly, the recess may have an insertion ramp.

According to a further embodiment of the invention, the locking element is preloaded via the clamping element in the locking position or unlocking position. The preload in the locking position ensures the securing of the base element in the chassis. As an alternative to active locking of the locking element via the clamping element, it is possible for the clamping element on the base element or the chassis to be displaced into the locking position via a spring element, and for the clamping element to move the locking element into the unlocking position for disassembly. When the base element is mounted to the chassis, the clamping element is actuated and the blockage of the locking element is removed, so that the locking element is displaced into the locking position by the restoring force of the spring element or elastomer element. The clamping element can support the preload in the locking position.

The locking element can be displaceably mounted in a direction transverse to a displacement direction of the clamping element, for example, via a gear drive, a thread, or via displacement. If, for example, the clamping element is formed as a screw, the locking element may be provided with an inclined or rounded contact surface, so that when the screw is displaced longitudinally, the locking element is displaced transversely to the displacement direction of the clamping element. The displacement of the locking element then results in a form-fitting and/or clamping locking of the longitudinal guide.

The locking element may be designed such that it can be slid or displaced into a receptacle or guide within the chassis. Preferably, the mounting of the locking element on the base element or the chassis is configured such that the locking element is not lost when the base element is disassembled. The locking element is formed as a module with the base or chassis.

The locking element can be formed as a ball or cone or has at least one rounded area that presses against the tongue or the groove wall of the longitudinal guide. This creates a high surface pressure or, when engaged in a recess, causes self-centering and orientation as well as automatic compensation of play.

While in previous systems more or less many additional components of a prosthetic hand have to be removed for a repair, said components not being connected to the actual finger to be disassembled, the present invention allows simple assembly or disassembly of prosthetic fingers. With the integrated design of the clamping element and, if applicable, the locking element in the chassis or the base element, it is no longer necessary to disassemble or deposit any components; rather, all components required for locking the base element to the chassis are integrated in the chassis or the base element. For example, the longitudinal guide groove may be formed or arranged on a wall of the chassis or on an edge of the chassis. The chassis wall forms a receiving cavity for electronic and/or mechanical components of the prosthetic hand, for example, motors, energy storage devices, control devices, sensors, mechanical components, energy storage devices, and the like. The cavity is milled or machined out of a solid base body, for example, and is closed after the mechanical components have been mounted. Only feedthroughs for actuating the prosthetic fingers are still present. This enables a simple construction of the chassis. A corresponding design is provided for in a chassis with an edge without a cavity.

A clamping element is arranged on the base element in a bore and in a thread, said clamping element displacing a locking element in such a way that the originally free translational degree of freedom required to insert the base element into the groove on the chassis is locked. At the same time, the base element is clamped and adjusted in the groove so that manufacturing tolerances can be selected to be large. The locking element is designed, for example, as a ball arranged outside the center axis of the threaded hole. A grub screw with a tapered tip can be used as the clamping element, said screw displacing the spherical locking element transverse to the longitudinal extension of the screw and the longitudinal guide when the screw penetrates the thread and presses it into a dome-shaped recess inside the groove wall. Therefore, only a single screw needs to be operated for assembly and disassembly, and no further components are required. In principle, it is also possible to arrange the groove and the tongue of the longitudinal guide in reverse, i.e. to design the groove in the base element and the tongue in or on the chassis. Likewise, it is possible to arrange the clamping element on the chassis, either in the tongue or next to the groove.

The longitudinal guide allows the base element to be fixed to the chassis with high strength and stability. While the usual fastening via screws or bolts quickly reaches the limits of stability due to the limited installation space and material failure often occurs, high forces can be easily absorbed via the longitudinal guide due to the large surfaces and stable design. In particular, if the insertion opening of the longitudinal guide is possible from the palm side, i.e. the displacement takes place in the dorsal direction, and one or more end stops are arranged or formed on the groove and the tongue, the forces usually acting in the dorsal direction can be absorbed very well. Tensile and compressive forces acting in the proximal and distal directions are effectively absorbed via the large surfaces of the longitudinal guide, so that only comparatively low surface pressures occur there.

In the case of multiple prosthetic fingers, which are fastened to the chassis accordingly via the longitudinal guide, each finger unit consisting of prosthetic finger and base part forms a unit which can be assembled and disassembled independently of one another. No hole is required in the chassis as a feedthrough to the chassis due to the design of the longitudinal guide with a closed groove.

Figure 2:
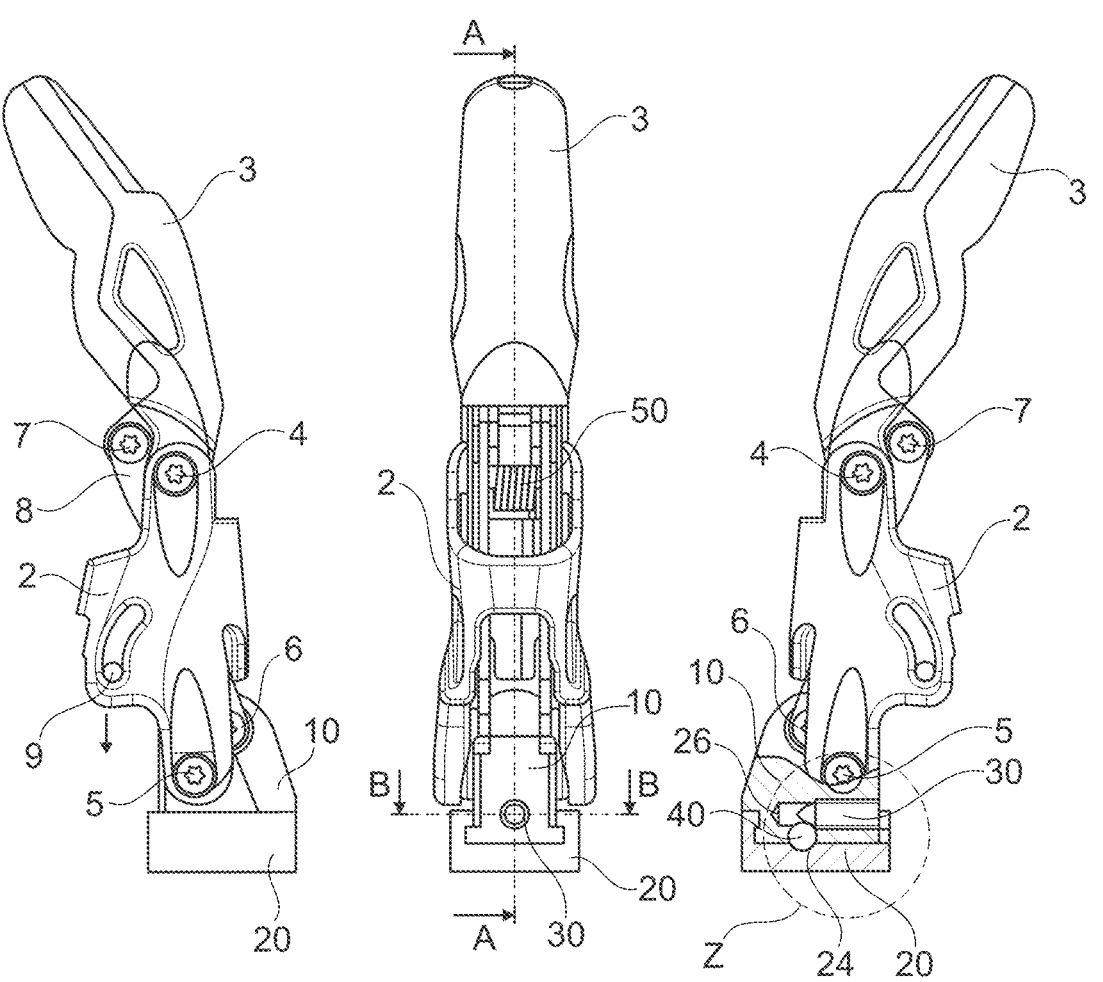
Figure 3:
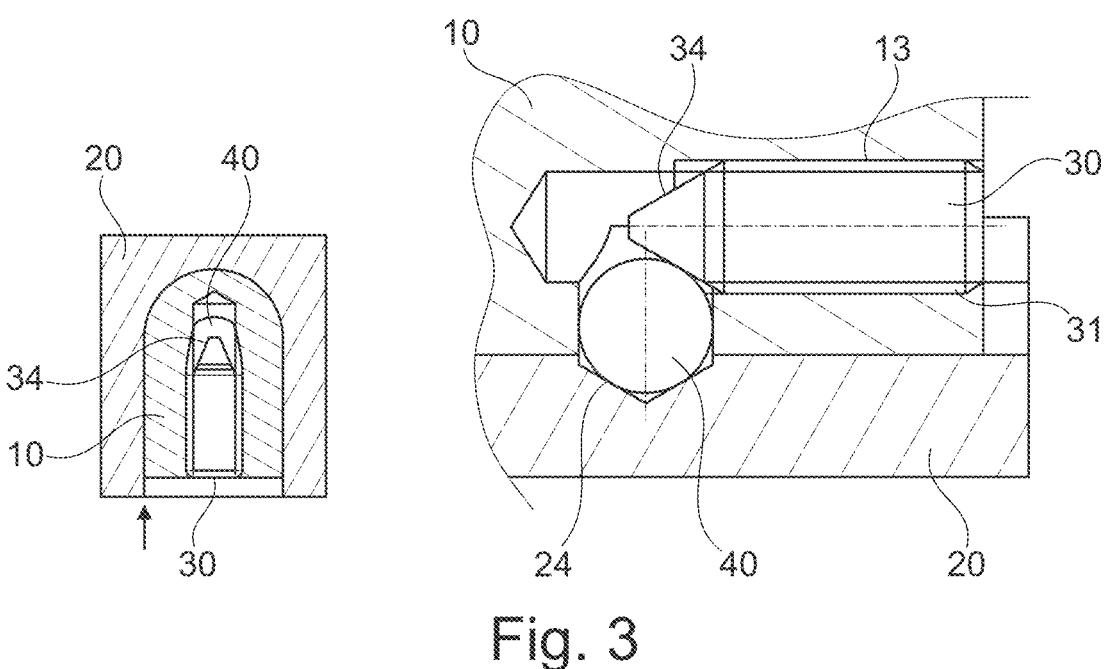
Figure 4:
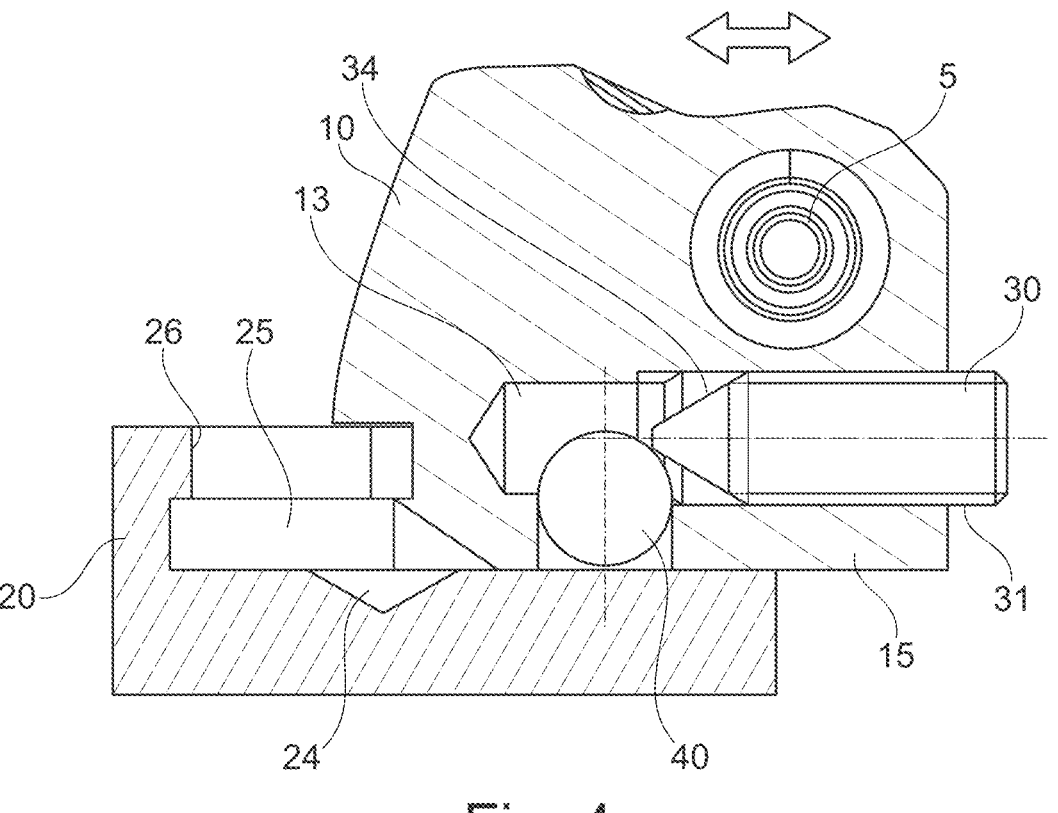
Figure 5:
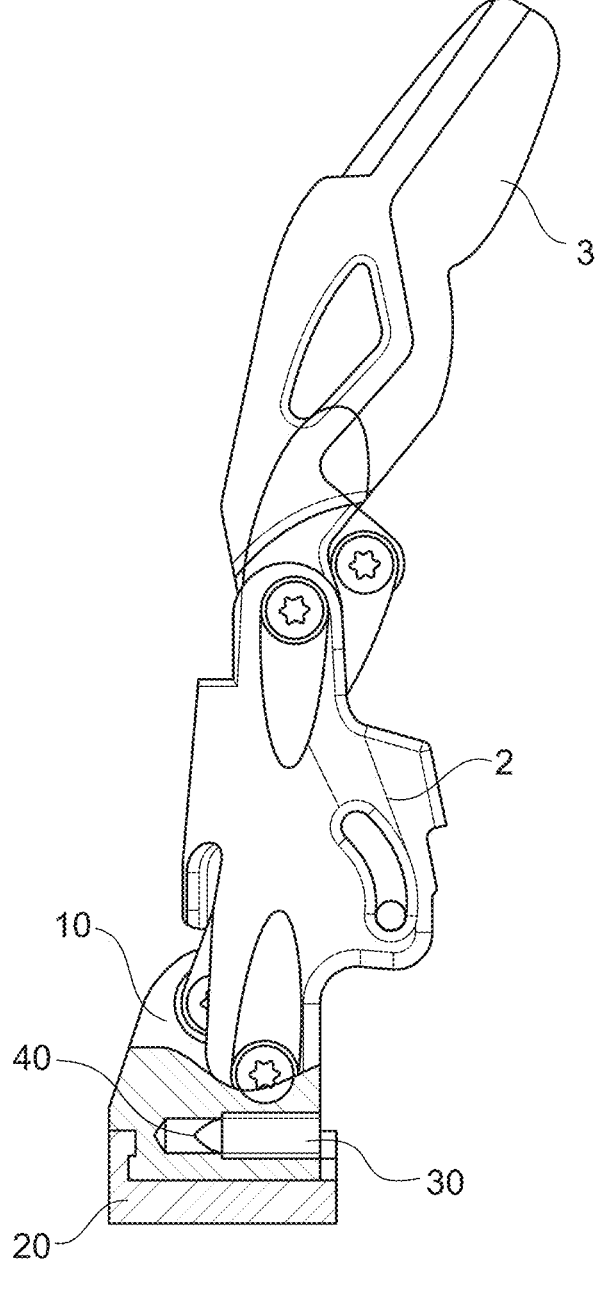
Figure 6:
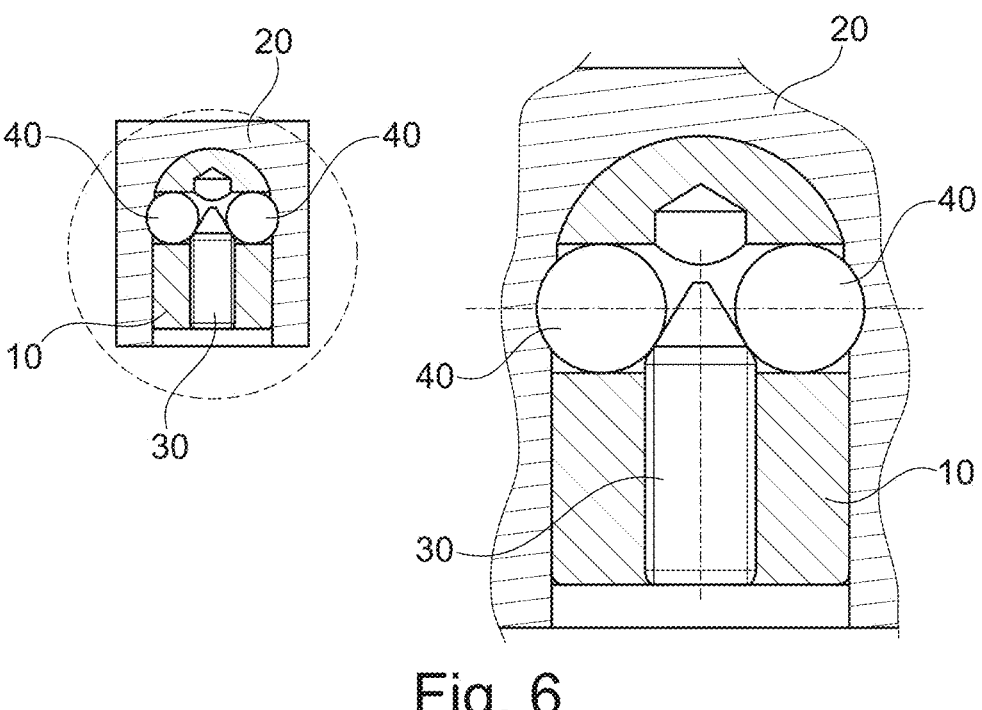

In the following, an embodiment example of the invention is explained in more detail with reference to the attached figures. They show:

FIG. 1—an extension view of a finger unit with prosthetic finger and base element as well as a part of a chassis;

FIG. 2—several views of an assembled prosthetic finger;

FIG. 3—two sectional views of the detail Z and according to B-B of FIG. 2 in the locked state;

FIG. 4—a sectional view according to FIG. 3 in the released state;

FIG. 5—a variant of FIG. 2;

FIG. 6—a variant of FIG. 3 with two locking elements; and

Figure 7:
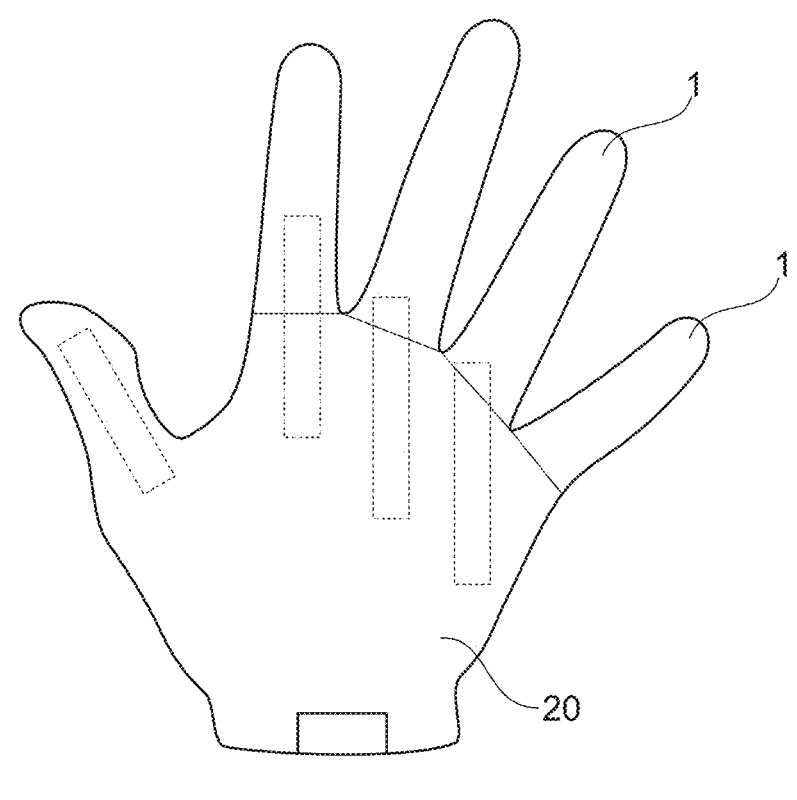

FIG. 7—a schematic representation of a prosthetic hand.

FIG. 7 shows a schematic representation of a prosthetic hand in which a plurality of prosthetic fingers 1 are arranged on a chassis 20 corresponding to the palm of a natural hand. The prosthetic fingers 1 are interchangeably mounted on the chassis 20. Motors, control devices, gears, and the like may be arranged within the chassis or on the chassis 20 to displace the prosthetic fingers 1 relative to the chassis 20. The chassis 20 may be attachable, particularly detachably attachable, to a forearm tube or a forearm socket. Electrical connections may lead from the chassis 20 into the prosthetic fingers 1, as may mechanical power transmission devices, such as levers, push rods, pull rods or cables, straps, belts or the like.

FIG. 1 shows a detailed view of a finger unit comprising the prosthetic finger 1 with a base element 10 and a partial view of the chassis 20. The prosthetic finger 1 has a proximal phalanx 2 or a distal phalanx 3, which are articulated to each other via a pivot axis 4. The proximal end of the proximal phalanx 2 is fixable to a base element via a pivot axis 5. Bearing axes 6 and 7 are arranged on different sides of the connecting line between the two pivot axes 4 and 5, said bearing axes being coupled to each other via a lever 8. The bearing axis 7 on the distal phalanx 3 is arranged volarly, the bearing axis 6 on the proximal phalanx 2 is arranged dorsally of the connecting line.

A bearing block is formed on the base element 10 with two bores 11, 12, which are arranged at a distance from one another. The proximal bearing bore 12 serves to receive the pivot axis 5, while the distal, dorsally arranged bearing bore 11 serves to receive the bearing axis 6. If the proximal phalanx 3 is pivoted about the bearing axis in the dorsal direction to close the hand, for example by a traction means engaging in recesses on the proximal phalanx 2, this leads to a displacement of the bearing axis 7 relative to the pivot axis 4 due to the distance between the two axes 5, 6, so that the distal phalanx 3 is flexed. In a reverse movement, an extension of the distal phalanx 3 occurs.

A tongue 15 is also formed on the base element 10 as part of a longitudinal guide. The tongue 15 has a substantially T-shaped cross-section and is formed at the proximal end of the base element 10. A suitably shaped plate could be attached to the underside of the base element 10 as an alternative embodiment to form such a tongue 15. The tongue 15 is configured to be inserted into a groove 25 of the base 20. The cross-section of the groove 25 corresponds to the cross-section of the tongue 15. An end stop 26 is formed at the dorsal end of the groove 25, so that the base element 10 can only be inserted up to this end. Seen from above, the groove 25 is rounded at the dorsal end; other shapes are also possible. Likewise, deviating cross-sectional shapes of the longitudinal guide are possible. In addition to a dovetail guide or an L-shaped guide, all longitudinal guides can be provided which block two translational degrees of freedom and, advantageously, all rotational degrees of freedom between the chassis 20 and the base element 10.

A bore 13 with an internal thread is formed within the base element 10, into which a clamping element 30 in the form of a grub screw with an external thread can be screwed. The tip of the clamping element 30 is tapered and acts on a locking element 40, which is mounted within a further bore or guide in the base element 10. The recess may be formed as a transverse bore to the bore 13 in the base element 10. To prevent the locking element 40, which in the illustrated embodiment is formed as a ball, from falling out, a grease filling or other securing device may be incorporated or arranged on the base element 10.

A corresponding recess for receiving the locking element 40 may be formed on the underside of the groove 25, for example a dome-shaped or conical recess.

In the illustrated embodiment, the groove 25 is milled or machined out of a solid material of the chassis 20. Alternatively, the groove 25 may be formed in multiple pieces by arranging a suitably shaped plate with recesses over a base groove.

FIG. 2 shows three representations of an assembled prosthetic finger 1 on the chassis 20. The left representation shows a side view with the chassis 20 and the base element 10 mounted in the groove. When a tensile force is applied in the direction of the arrow to a coupling element 9, which is arranged in a corresponding guide within the proximal phalanx 2, the proximal phalanx 2 pivots about the pivot axis 5. The lever 8 remains fixed to the bearing axis 7 and rotates counterclockwise together with the proximal phalanx 2, but only about the proximal bearing axis 6. The pivot axis 4 as well as the bearing axis 7 also pivot counterclockwise, and the distal phalanx 3 also pivots about the pivot axis 4 due to the rigid coupling between the two bearing axes 6, 7, which allow pivotable displacement. A reset can be achieved via an opposing displacement of the proximal phalanx 2 or a spring. An actuator may be arranged on the dorsal side of the chassis 20, possibly in a recess delimited by a chassis wall.

In the middle representation of FIG. 2, a dorsal view of the prosthetic finger is shown. The chassis 20 is only partially shown. It can be seen that the base element is inserted within the groove 25 in the chassis 20. The base element 10 has an essentially T-shaped cross-section, so that it can be inserted into the correspondingly formed groove 25. After insertion, before the clamping element 30 activates and the locking element 40 causes locking, the base element 10 is already restricted in two translational degrees of freedom, and movements perpendicular to the insertion direction are locked. A spring 50 can be seen on the inner side of the prosthetic finger 1, said spring causing an extension of the distal phalanx 3 relative to the proximal phalanx 2 in the extension direction. If a tensile force is no longer exerted by the coupling element 9, the restoring force of the spring 50 causes an extension and thus a return to the starting position.

A sectional view according to A-A is shown in the right-hand representation of FIG. 2. In particular, it can be seen from detail Z that the base element 10 is inserted completely, up to an end stop 26, in the groove 25 with the bearing block for the two axes 5, 6 projecting distally beyond the chassis 20. The clamping element 30 is screwed into the thread of the bore 13 and acts on the locking element 40, which is pressed onto the bottom of the groove 25 into a recess 24. The recess 24 may be dome-shaped or conical, so that if the base element 10 is not fully inserted, it will automatically self-center and self-align within the chassis 20. By screwing the clamping element 30 in the dorsal direction, the locking element 40 in the form of the ball is pressed into the recess 24 in the proximal direction. This locks the tongue 15 within the groove 25 in a form-fitting manner and, in addition, results in clamping at the upper edge of the T-shaped groove. The base 10 and thus the prosthetic finger 1 are thus mounted free of play and stably within the groove 25 on the chassis 20. High holding forces can be achieved by this type of locking, since large contact surfaces are available to absorb compressive forces and tensile forces. Displacement in the dorsal direction, i.e. towards the back of the hand, is prevented by the solid end stop 26, so that very high compressive forces can be absorbed in the dorsal direction. The compressive forces in the volar direction are generally much lower and lead to buckling of the prosthetic fingers, which is indicated by the elongated hole guide for the coupling element 9.

In FIG. 3, the left-hand representation shows the section B-B and the right-hand representation shows the detail Z. In the left-hand representation, it can be seen that the clamping element 30 acts on the locking element 40 and presses the latter downwards towards the closed bottom surface of the groove 25 of the base part 20 due to the conical tip 34. Both the clamping element 30 and the base element 10 are displaced in the same direction, so that assembly can take place very easily from the palm side or from the volar side in the dorsal direction.

A sectional view in the right-hand representation of FIG. 3 shows that the spherical locking element 40 is pressed into the conical recess 24 by the tapered tip 34 of the locking element 30. The clamping element 30 is provided with an external thread 31 which engages the internal thread of the bore 13. Even if the screw or locking element 30 is partially unscrewed, it will continue to remain permanently attached to the base element 10. The locking element 40 can be held in a grease bearing, by a magnetic force, or by a retaining ring on the underside or other suitable retaining device within the downward bore to receive the locking element 40 and secure it against falling out, as explained above.

In FIG. 4, the arrangement comprising the base element 10 and the chassis 20 is shown in a sectional view according to detail Z in a non-assembled state. The clamping element 30 is partially unscrewed from the base element 10, and the locking element 40 is received within the bore 13 and does not extend beyond the underside of the tongue 15. The base element 10 can be moved within the groove 25 in the insertion and removal directions indicated by the double arrow. The prosthetic finger, which is not shown, is already ready-mounted to the base element 10 via the pivot axis 5 and can be fixed together with it as a module to the chassis 20. To fix it, the base element 10 is fully inserted up to the end stop 26. The transverse bore for the locking element 40 then lies essentially corresponding to the recess 24. The clamping element 30 is then screwed in, and the cone 34 presses the locking element 40 down into the recess 24, resulting in a form-fit and clamping locking of the base element 10 within the chassis 20. To release, the clamping element 30, which is in the form of a grub screw, is unscrewed so that the locking element can be moved into the bore 13, thereby removing the clamping action and form-fit locking. The prosthetic finger 1 can then be removed together with the base element 10, if necessary after decoupling the coupling element 9 from the chassis 20.

FIG. 5 shows a variant of the attachment, FIG. 5 corresponding to the right-hand representation of FIG. 2. The basic structure is the same, alternatively to being clamped to the base of the groove 25, the locking element 40 is arranged in a plane parallel to the base surface of the groove 25 and thus acts on a side surface of the groove 25. If there is only one locking element 40, the tongue 15 is pressed in the opposite direction. If two locking elements are present, a central self-centering occurs.

In FIG. 6, the embodiment with two locking elements 40 is shown, the left representation corresponds to the left representation of FIG. 4, accordingly, the right representation corresponds to the right representation of FIG. 4. It can be seen that two locking elements 40 are arranged opposite each other in a transverse bore within the base element 10. The transverse bore is orthogonal to the bore 13 and to the direction of insertion of the clamping element 30. The conical tip 34 acts on both locking elements 40 and presses them outwardly into recesses or only against the side wall of the groove 25.

Alternatively, it is possible that one locking element is pressed into the bottom surface or into the base surface of the groove 25 and the other locking element 40 is pressed against a side wall of the groove 25. In principle, it is also possible that three locking elements 40 are provided, two interacting with the side surfaces of the groove, one with the bottom surface.

In principle, it is also possible that the locking element and the clamping element are arranged in the chassis and act on the tongue in the base element. A recess can then be arranged in the tongue. In principle, it is also possible for the clamping element to directly effect a clamping and/or form-fit locking. Likewise, a kinematic reversal is possible, i.e., the design of the groove within the base element and the tongue within or on the chassis.

The invention claimed is:

1. A prosthetic hand, comprising:
    a chassis;
    at least one base element for fastening a prosthetic finger to the chassis;
    a longitudinal guide for the at least one base element arranged or formed on the chassis, wherein the at least one base element is mounted in said longitudinal guide, wherein the longitudinal guide blocks two translatory degrees of freedom; and
    a clamping element assigned to the longitudinal guide, wherein said clamping element is displaceably mounted in or on the chassis or the at least one base element between a locking position and an unlocking position, and wherein the clamping element effects a blocking of a third translational degree of freedom in the locking position, wherein the longitudinal guide has at least one end stop.

2. The prosthetic hand according to claim 1, wherein the clamping element acts on at least one locking element and brings the at least one locking element from an unlocking position into a locking position or vice versa.

3. The prosthetic hand according to claim 2, wherein either the clamping element or the at least one locking element is assigned a recess in which the clamping element or the at least one locking element engages in the locking position.

4. The prosthetic hand according to claim 3, wherein the recess is arranged at a position in which the at least one base element assumes an end position on the chassis.

5. The prosthetic hand according to claim 2, wherein the at least one locking element is preloaded via the clamping element in the locking position or unlocking position.

6. The prosthetic hand according to claim 2, wherein the at least one locking element is mounted displaceably in a transverse direction to a displacement direction of the clamping element.

7. The prosthetic hand according to claim 2, wherein the at least one locking element is mounted in a receptacle or guide such that it can be relocated or displaced.

8. The prosthetic hand according to claim 2, wherein the at least one locking element is designed as a ball or cone or has at least one rounded region.

9. The prosthetic hand according to claim 1, wherein the clamping element or the at least one locking element clamps and/or locks the at least one base element in the longitudinal guide in a form-fitting manner.

10. The prosthetic hand according to claim 1, wherein the longitudinal guide is designed as a T-guide, L-guide, cylinder guide or dovetail guide.

11. The prosthetic hand according to claim 1, wherein the at least one base element has a bearing block for the prosthetic finger.

12. The prosthetic hand according to claim 1, wherein the clamping element is displaceably mounted along a longitudinal extension of the longitudinal guide.

13. The prosthetic hand according to claim 1, wherein the clamping element is designed as a screw or is coupled to a screw.

14. A prosthetic hand, comprising:
    a chassis;
    at least one base element for fastening a prosthetic finger to the chassis;
    a longitudinal guide for the at least one base element arranged or formed on the chassis, wherein the at least one base element is mounted in said longitudinal guide, wherein the longitudinal guide blocks two translatory degrees of freedom; and
    a clamping element assigned to the longitudinal guide, wherein said clamping element is displaceably mounted in or on the chassis or the at least one base element between a locking position and an unlocking position, and wherein the clamping element effects a blocking of a third translational degree of freedom in the locking position,
    wherein the clamping element acts on at least one locking element and brings the at least one locking element from an unlocking position into a locking position or vice versa
    wherein the at least one locking element is mounted displaceably in a transverse direction to a displacement direction of the clamping element.

15. The prosthetic hand according to claim 14, wherein the clamping element or the at least one locking element clamps and/or locks the at least one base element in the longitudinal guide in a form-fitting manner.

16. The prosthetic hand according to claim 14, wherein the longitudinal guide is designed as a T-guide, L-guide, cylinder guide or dovetail guide.

17. The prosthetic hand according to claim 14, wherein the at least one base element has a bearing block for the prosthetic finger.

18. The prosthetic hand according to claim 14, wherein the clamping element is displaceably mounted along a longitudinal extension of the longitudinal guide.

19. The prosthetic hand according to claim 14, wherein either the clamping element or the at least one locking element is assigned a recess in which the clamping element or the at least one locking element engages in the locking position.

20. The prosthetic hand according to claim 19, wherein the recess is arranged at a position in which the at least one base element assumes an end position on the chassis.

\* \* \* \* \*